(12) United States Patent
Barker et al.

(10) Patent No.: US 6,509,161 B1
(45) Date of Patent: Jan. 21, 2003

(54) GREEN FLUORESCENT PROTEIN

(75) Inventors: Michael Gordon Barker, Manchester (GB); Nicholas Billinton, Manchester (GB); Nicholas John Goddard, Warrington (GB); Richard Maurice Walmsley, Manchester (GB); Andrew William Knight, Manchester (GB); Peter Robert Fielden, Bury (GB)

(73) Assignee: Gentronix Limited, Manchester (GB)

( * ) Notice: Subject to any disclaimer, the term of this patent is extended or adjusted under 35 U.S.C. 154(b) by 0 days.

(21) Appl. No.: 09/514,994

(22) Filed: Feb. 29, 2000

(51) Int. Cl.$^7$ ................................. G01N 33/53
(52) U.S. Cl. .................. 435/7.1; 435/7.1; 435/4; 530/350; 530/300; 436/517
(58) Field of Search ................. 530/350, 300; 435/7.1, 4; 436/517

(56) References Cited

FOREIGN PATENT DOCUMENTS

WO    WO 98/44149    10/1998

OTHER PUBLICATIONS

Hadjantonakis et al., Histochem. Cell Biology, vol. 115, No. 1, pp. 49–58, 2001.*
Plautz et al., Gene, vol. 173, pp. 83–87, 1996.*
Knight et al., Anal. Commun., vol. 36, pp. 113–117, 1999.*
Quantitative imaging of green fluorescent protein in cultured cells: comparison of microscopic techniques, use in fusion proteins and detection limits, K.D. Niswender et al., Journal of Microscopy, vol. 180, Pt. 2, Nov. 1995, pp. 109–116.

* cited by examiner

Primary Examiner—Karen Cochrane Carlson
Assistant Examiner—Hope A. Robinson
(74) Attorney, Agent, or Firm—Woodard Emhardt, Naughton, Moriarty & McNett (57) ABSTRACT

A method of distinguishing between fluorescent light emitted by green fluorescent protein and fluorescent light emitted by auto-fluorescent molecules, the method comprising:

using plane-polarised light to illuminate a sample containing green fluorescent protein and auto-fluorescent molecules;

detecting the intensity of fluorescent light that is emitted with a first polarisation from the sample;

detecting the intensity of fluorescent light that is emitted with a second polarisation from the sample; and subtracting a first of said detected intensities from a second of said detected intensities to obtain a difference signal.

19 Claims, 7 Drawing Sheets

GREEN FLUORESCENT PROTEIN

FIELD OF THE INVENTION

The present invention relates to a method and apparatus for the detection of Green Fluorescence Protein GFP).

BACKGROUND TO THE INVENTION

GFP is found in the jellyfish *Aequorea victoria*. With the ability to clone and express GFP in a diverse range of cells and organisms including bacteria, yeast, plants and higher animals, GFP has become a versatile fluorescent marker for monitoring physiological processes, visualising protein localisation and detecting the expression of transferred genes [*Green Fluorescent Proteins, Proteins, Properties, Applications and Protocols*, ed. M. Chalfie and S. Kain, Wiley and Sons, 1$^{st}$ edn., 1998; H-H Gerdes and C. Kaether, *FEBS Lett.*, 1996, 389, 44; A. B. Cubitt, R. Heim, S. R. Adams, A. E. Boyd, L. A. Gross and R. Y. Tsien, *Trends Biol. Sci.*, 1995, 20, 448]. The usefulness of GFP stems from the fact that fluorescence from GFP requires no additional co-factors; the fluorophore is self-assembling via a cyclization reaction of the peptide backbone.

GFP is bio-compatible, and when used as a tag does not alter the normal function or localisation of a protein to which it is fused. Proteins, cells and organelles marked with GFP can be visualised and monitored in living tissue without the need for fixation. Hence the dynamics of cellular processes can be non-invasively quantified in real time using GFP, simply by the measurement of fluorescence.

The wild-type GFP consists of 238 amino acids and has a cylindrical structure with the fluorophore element encapsulated in the centre [F. Yang, L. G. Moss and G. N. Phillips, Jr., *Nat. Biotechol.*, 1996, 14, 1246]. As such it is a very chemically and photochemically stable and resilient fluorophore. Bright green fluorescence at 508–515 nm is readily induced by illumination of GFP with visible blue light at 470 nm. Genetic modification of GFP has been used to provide several useful mutants with fluorescence that is significantly blue or yellow shifted.

One application of GFP is in the development of an automated flow-injection bioassay for the detection of genotoxic compounds and the quantification of genotoxicity. The basis of the method is the use of yeast cells that are genetically modified such that they produce GFP in response to the activation of the cells' DNA repair mechanisms by DNA damage. The presence, concentration or potency, of a suspected genotoxic compound can be quantified by measuring an increase in green fluorescence from intact yeast cells [R. M. Walmsley, N. Billinton and W.-D. Heyer, *Yeast*, 1997, 13, 1535; N. Billinton, M. G. Barker, C. E. Michael, A. W. Knight, N. J. Goddard, P. R. Fielden and R. M. Walmsley, *Biosens. Bioelectron.*, 1998, 13, 831; A. W. Knight, N. J. Goddard, P. R. Fielden, M. G. Barker, N. Billinton and R. M. Walmsley, *Meas. Sci. Technol.*, 1999, 10, 211].

Organs or organelles within organisms or cells where GFP is localised can often be readily visualised and distinguished from the background matrix by fluorescence microscopy techniques. However, in cases where GFP is only weakly expressed, or where GFP is in free solution such as in the cell cytosol, the fluorescence signal from GFP is invariably contaminated by cellular or media auto-fluorescence [K. D. Niswender, S. M. Blackman, L. Rohde, M. A. Magnuson and D. W. Piston, *J. Microsc.*, 1995, 180, 109]. This has also been the case in yeast cell studies. In an analytical context this restricts the lower limit of detectable signal.

The term auto-fluorescence refers to fluorescence arising from any species other than GFP, known or unknown, naturally occurring or added, which is significantly bright at the wavelength of GFP fluorescence.

Green auto-fluorescence is almost universal to all living cells and organisms, and arises from a diverse range of sources. Likely chemical sources are reduced nicotinamide dinucleotides, oxidised flavins, age-related pigments and oxidised aromatic amino acids such as tryptophan. However, in many cases the exact source of auto-fluorescence is unknown. In general the brightness of the auto-fluorescence increases with the age of the cell or organism. Lipofuscins is a general term name for the auto-fluorescence that accumulates in (particularly ageing) mammalian cells. Auto-fluorescence has been noted to cause difficulties in the quantification of GFP expressed in many cells and species, for example:

Mammalian Heart Cells (Auto-fluorescence arising from myocardium); T. Kawada, W. S. Shin, Y. Nakatsuru, T. Koizumi, A. Sakamoto, T. Nakajima, Y. OkaiMatsuo, M. Nakazawa, H. Sato, T. Ishikawa, T. ToyoOka. Precise identification of gene products in hearts after in vivo gene transfection, using sendai virus-coated proteoliposomes. *Biochemical and Biophysical Research Communication*, 1999, 259, 408.

Plants (Auto-fluorescence arising from cell walls in maize plants); A. H. M. vanderGeest, J. F. Petolino. Expression of a modified green fluorescent protein gene in transgenic maize plants and progeny. *Plant Cell Reports*, 1998, 17, 760.

Nematodes (Roundworms) (Auto-fluorescence mainly from the gut); S. Hashmi, M. A. AbuHatab, R. R. Gaugler. Green fluorescent protein a versatile gene marker for entomopathogenic nematodes, *Fundamental and Applied Nematology*, 1997, 20, 323; *Green Fluorescent Proteins: Proteins, Properties, Applications and Protocols*, ed. M. Chalfie and S. Kain, Wiley and Sons, 1$^{st}$ edn., 1998, p. 154.

Drosophila (Fruit flies); J. D. Plautz, R. N. Day, G. M. Dailey, S. B. Welsh, J. C. Hall, S. Halpain, S. A. Kay. *Green fluorescent protein and its derivatives as versatile markers for gene expression in living Drosophila melanogaster*, plant and mammalian cells. *Gene*, 1996, 173, 83; *Green Fluorescent Proteins: Proteins, Properties, Applications and Protocols*, ed. M. Chalfie and S. Kain, Wiley and Sons, 1$^{st}$ edn., 1998, p. 172.

Bacteria; P. J. Lewis, J. Errington. Use of green fluorescent protein for detection of cell-specific gene expression and subcellular protein localization during sporulation in *Bacillus subtilis. Microbiology-UK*, 1996, 142, 733.

Yeast; Green Fluorescent Proteins: Proteins, Properties, Applications and Protocols, ed. M. Chalfie and S. Kain, Wiley and Sons, 1$^{st}$ edn., 1998, p. 149.

Many methods have been used to reduce the effect of auto-fluorescence upon GFP measurements, with varying degrees of success. However, each of the known methods suffers from disadvantages.

A first known method of reducing the effect of auto-fluorescence upon GFP measurements involves designing an optimised set of optical narrow-band filters to specifically pick out regions of the optical spectrum where GFP can be both excited, and emit light, with greater efficiency than the auto-fluorescence (see for example M. J. Zylka and B. J. Schnapp. Optimized filter set and viewing conditions for S65T mutant of GFP is living cells. *Biotechniques*, 1996, 21, 220). In most applications, the standard optical filter sets for fluorescein are not specific enough to discriminate GFP from auto-fluorescence. Dedicated excitation and emission filter sets for GFP have recently been made commercially available, although they are not suitable for all existing instrumentation. These filter sets suffer from the disadvantage that they are currently relatively expensive at several hundred pounds sterling per set. A further disadvantage is that in many cases the excitation and emission spectra of the auto-fluorescence significantly overlap those of GFP, making it difficult to distinguish between GFP fluorescence and auto-fluorescence signals.

Most researchers are required to optimise their own set of filters, using filters from various commercial sources, for their own particular applications. This is for two main reasons. Firstly, auto-fluorescence arises from a disparate, and often unknown range of chemicals, and varies enormously between different cells and species, and even over the lifetime of an individual cell. Secondly, new GFP mutants with diverse spectroscopic properties are becoming available all the time.

It should be noted the greatest wavelength discrimination achievable using optical narrow-band filters is by the use of multiple overlapping filters. However, where this is done a significant proportion of the available fluorescence signal is lost with each filter, (typically 30 to 50%), hence reducing measurement sensitivity.

Enhanced measurement of GFP can be made under a microscope by selectively focussing on one small, defined area of a specimen without illuminating the whole sample. This can be achieved in three dimensions using confocal fluorescence microscopy (see for example G. Jung, J. Wiehler, W. Göhde, J. Tittel, Th. Basché, B. Steipe, C. Br äuchle. Confocal microscopy of single molecules of the green fluorescent protein. *Bioimaging*, 1998, 6, 54; K. D. Niswender, S. M. Blackman, L. Rohde, M. A. Magnuson, D. W. Piston. Quantitative imaging of green fluorescent protein in cultured cells: comparison of microscopic techniques, use in fusion proteins and detection limits. *Journal of Microscopy*, 1995, 180, 109). In a typical arrangement, laser light is reflected by a dichroic mirror and focussed onto a sample by a microscope objective. The emitted fluorescence is collected by the same objective, passes through the dichroic mirror and is spatially filtered from background light by a pinhole (typically a few 100 μm in diameter) located in front of the detector. This approach is useful where auto-fluorescence arises from a distinct subcellular component, such as a cell wall.

A disadvantage of this approach is the requirement for complex and expensive instrumentation. Furthermore, confocal fluorescence microscopy will not completely eliminate auto-fluorescence when that auto-fluorescence is dispersed throughout the sample, or when that auto-fluorescence operates at the same wavelength as GFP. Confocal fluorescence microscopy is most suited for the discrimination of GFP from auto-fluorescence sources which are located away from the focal spot of a microscope.

In a further method of reducing auto-fluorescence, known as two photon excitation spectroscopy, short pulses of near infra-red laser light (typically 100 femto seconds at 100 MHz) are focused onto a sample in the same manner as described above in relation to confocal microscopy (see for example K. D. Niswender et al. (as above); S. M. Potter, C.-M. Wang, P. A. Garrity, S. E. Fraser. Intravital imaging of green fluorescent protein using two-photon laser-scanning microscopy. *Gene*, 1996, 173, 25). Two-photon excitation occurs on simultaneous absorption of two separate photons, each having half the energy required to cause transition to the excited state. (For example 780 nm light is used to excite a transition that would be excited by light at 390 nm).

Excitation only occurs within a diffraction, limited focal spot, with virtually no fluorescence excitation above or below the focal plane. Hence, a confocal pinhole is not required for spatial resolution and a greater amount of light can be collected than is collected using confugal fluorescence microscopy, thus enhancing the sensitivity of the technique. Any reflected infra-red excitation light is easily removed from the fluorescence emission signal, since it is separated in wavelength from the fluorescence.

Two photon excitation spectroscopy has several disadvantages. The first is the need for complex and expansive instrumentation (pulsed lasers, etc.). The second is that common wavelengths from infra-red lasers tend produce excitation at wavelengths below 490 nm, where the effect of auto-fluorescence increases due to efficient excitation of NADH (which is abundant in cells). A further disadvantage of two photon excitation spectroscopy is the rapid photobleaching of GFP.

Time resolved fluorescence spectroscopy (TRFS) and fluorescence lifetime imaging microscopy (FLIM), are often used to quantify or visualise fluorescent labels in the presence of background non-specific auto-fluorescence. This approach is successful, provided that the fluorescence lifetime of a label is significantly longer than that of the auto-fluorescence (see for example R. Pepperkok, A. Squire, S. Geley, P. I. H. Bastiaens. Simultaneous detection of multiple green fluorescent proteins in live cells by fluorescence lifetime imaging microscopy. *Current Biology*, 1999, 9, 269). A pulsed light source is used, and fluorescence of the label is measured a set time after the short-lived auto-fluorescence has decayed. Common labels are based on osmium, ruthenium or lanthanide chelates, with fluorescence lifetimes typically 20 ns or more.

Since GFP has a particularly short fluorescence lifetime (approximately 2.8 ns) this approach is not particularly useful in the discrimination of GFP and auto-fluorescence. In addition, the method requires complex and expansive instrumentation. FLIM has however been used to distinguish different GFP's in a multiple labelling application, using the diversity in individual GFP mutant's fluorescence lifetimes.

Auto-fluorescence in microscopy images can sometimes be corrected for, either visually or by computer picture manipulations given sufficient, separation between the GFP fluorescence wavelength and the auto-fluorescence wavelength. For example, auto-fluorescence is often more yellow-green, rather than pure bright green in appearance. However, such transformations are subjective and inevitably involve corruption of an original image. Correction of this type requires the use of expensive colour detectors.

A further know approach to reducing media auto-fluorescence has been to irradiate a medium with short wavelength ultra-violet light before use (see for example M. J. Zylka et al., full reference given above). This photobleaches some components likely to cause autofluorescence. This approach suffers from the disadvantage that it may also destroy media components which are critical for sustaining cells, or may form photochemical derivatives harmful to cells. Culture media can be switched for UV-treated media just prior to measurement, although this necessitates an extra laborious step, and is not applicable to continuous real-time monitoring.

Some researchers have used genetics to solve specific auto-fluorescence problems, by restricting their selection of GFP mutants to those which have emission wavelengths significantly separated from those of the interfering autofluorescence, or which are exceptionally bright (see for example R. H. Kohler, W. R. Zipfel, W. W. Webb, M. R. Hanson.

The green fluorescent protein as a marker to visualize plant mitochondria in vivo. *Plant Journal*, 1997, 11, 613). In addition, very strong promoters are used such that the chosen GFP is highly expressed, or localised within parts of a cell. This is often used in applications where there is intense auto-fluorescence, such as in green plant tissues. In applications where GFP is not localised or only weakly expressed, the presence of natural auto-fluorescence severely restricts the usefulness of GFP with conventional fluorescence detection.

Many common growth media are highly auto-fluorescent. Researchers have therefore tried to reduce auto-fluorescence from this source by the use of selected minimal, defined media, notably with low concentrations of riboflavin and tryptophan. Such media suffer from the disadvantage that they often prove sub-optimum for cell growth and development compared to richer, more complex, media.

The commonly used S65T GFP mutant is fluorescent from pH 7 to 11.5, whereas some cellular auto-fluorescence is quenched at high pH. Hence it sometimes possible to increase pH (typically to pH 10–11) to reduce background auto-fluorescence (see for example R. M. Walmsley, N. Billinton, W.-D., Heyer. Green fluorescent protein as a reporter for the DNA damage-induced gene RAD54 in *Saccharomyces cerevisiae. Yeast*, 1997, 13, 1535). However, this is an invasive step which will be detrimental to living cells and is best applied to cellular extracts.

Capillary electrophoresis (CE) has been used to directly separate GFP from other auto-fluorescent proteins and intracellular components (see for example A. Malek, M. G. Khaledi. Expression and analysis of green fluorescent proteins in human embryonic kidney cells by capillary electrophoresis. *Analytical Biochemistry*, 1999, 268, 262; G. M. Korf, J. P. Landers, D. J. O'Kane. Capillary electrophoresis with laser-induced fluorescence detection for the analysis of free and immune-complexed green fluorescent protein. *Analytical Biochemistry*, 1997, 251, 210). CE is widely used in biomedical applications due to the small sample volumes required and rapid analysis time. CE is a high resolution separation technique in which molecules to be separated migrate in an electric field, with mobilites that depend on molecular size and charge. Separation takes place in a capillary tube across which a voltage of 10's of kV is applied. In the case of GFP, CE is coupled with laser fluorescence detection.

The technique works best for cellular extracts, however these must be laboriously prepared by washing and lysis of the cells, followed by centrifugation, filtration and re-suspension steps. Using CE it is possible to separate different forms of GFP, and bound from unbound GFP for example using antibody labels. Whole cells may be analysed, but only for separation from auto-fluorescent components arising from the growth medium.

CE is inherently destructive and requires expensive instrumentation (high voltage power supply, laser induced fluorescence detector). It can also be difficult to optimise the CE buffer conditions such as pH, to suit both the separation and GFP fluorescence, whilst in some cases also sustaining cells.

It is apparent from the above that the problem of how to reduce the effect of auto-fluorescence upon GFP measurements is well recognised, and that a wide variety of methods have been developed in order to try and minimise the effect of auto-fluorescence. All of the known methods suffer from significant disadvantages.

It is an object of the present invention to provide a method and apparatus for discriminating GFP and auto-fluorescence which overcomes at least some of the above disadvantages.

SUMMARY OF THE INVENTION

According to a first aspect of the invention, there is provided a method of distinguishing between fluorescent light emitted by green fluorescent protein and fluorescent light emitted by auto-fluorescent molecules, the method comprising:

using plant-polarised light to illuminate a sample containing green fluorescent protein and auto-fluorescent molecules;

detecting the intensity of fluorescent light that is emitted with a first polarisation from the sample;

detecting the intensity of fluorescent light that is emitted with a second polarisation from the sample; and subtracting a first of said detected intensities from a second of said detected intensities to obtain a difference signal.

The inventors have realised that a sample, when illuminated by polarised light, provides strongly polarised GFP fluorescence and significantly less polarised auto-fluorescence. The difference signal obtained according to the invention thus distinguishes between light emitted by GFP and light emitted by auto-fluorescent molecules. The invention provides a new and straightforward method for distinguishing GFP fluorescence from auto-fluorescence.

The term auto-fluorescent molecule is intended to include any molecule other than GFP, known or unknown, naturally occurring or added, which is significantly bright at the wavelength of GFP fluorescence.

A polarised light source may either produce polarised light directly, for example an argon ion laser, or may produce unpolarised light which is polarised upon passing through a polarising filter placed between the light source and the sample. Examples of suitable light sources include lasers, LED's, xenon lamps, mercury lamps and halogen lamps.

Any suitable detector may be used to detect the fluorescent light, For example, a photomultiplier tube detector, a silicon photodiode, a CCD camera, video camera, photographic film and the eye. One or more polarising filters may be used to select a particular polarisation of fluorescent light for detection.

The inventors have determined that for GFP in free solution, or contained within a cytosol of a yeast cell, the intensity of fluorescence perpendicularly polarised with respect to a polarised light source ($I_\perp$) is approximately 50% less than the intensity of fluorescence aligned parallel to the polarised light source $I_{\parallel}$).

Measured fluorescence polarisation (P) may be defined as follows:

$$P = (I_{\parallel} - I_{\perp})/(I_{\parallel} + I_{\perp})$$

The difference between $I_{\parallel}$ and $I_{\perp}$ is large for GFP fluorescence, since the GFP fluorescence is significantly polarised, but much less for background auto-fluorescence. Thus by measuring the difference signal ($I_{\parallel} - I_{\perp}$) it is possible to discriminate between GFP and auto-fluorescence, even when the GFP and auto-fluorescence occur at the same wavelength.

The inventors believe that the strong polarisation of GFP fluorescence arises as a result of the large size, and hence slow rotation rate, of GFP in solution. When fluorescent molecules are illuminated by plane polarised light, those molecules with an electronic transition moment aligned parallel to the electric vector of the excitation light are excited. Since GFP is a relatively large molecule and the fluorophore element of GFP is rigidly encapsulated within a cylindrical structure, the fluorophore element of GFP rotates at a rate which is slow compared to the rate at which it fluoresces (the fluorescence lifetime of GFP is approximately 2.8 ns [A. W. Knight, N. J. Goddard, P. R. Fielden, M. G. Barker, N. Billinton and R. M. Walmsley. *Anal. Commun.*, 1999, 36, 113; B. P. Cormack, G. Bertram, M. Egerton, N. A. R. Gow, S. Flakow and A. J. P. Brown, *Microbiology*, 1997, 143, 303]). Consequently, GFP fluorescence is strongly polarised parallel to the plane of polarisation of the illumination. In contrast to GFP, the molecules that give rise to auto-fluorescence are commonly smaller. Fluorescence emissions from such molecules are largely free of polarisation, since the molecules are free to rotate during the time taken for the electronic transitions of fluorescence emission to occur. In other words, the rotational relaxation time of the molecules is much shorter than the fluorescence decay time and the molecular orientation effectively becomes randomised before fluorescence occurs.

The method according to the first aspect of the invention will distinguish between fluorescent light emitted by green fluorescent protein and fluorescent light emitted by auto-fluorescent molecules, provided that the auto-fluorescent molecules emit fluorescent light that is less polarised than fluorescent light emitted by the green fluorescent protein (i.e. provided that the auto-fluorescent molecules emit fluorescent light with a lower polarisation ratio).

The inventors are aware of a paper that suggests that GFP can be used to replace fluorescein in many biochemical analyses [S. H. Park, R. T. Raines. Green fluorescent protein as a signal for protein-protein interactions. *Protein Science*, 1997, 6, 2344]. The paper describes monitoring a change of the polarisation of GFP fluorescence when GFP binds to an S-protein fragment of ribonuclease A. This change of polarisation is used to probe protein-protein interactions and obtain binding coefficients. However, although the method described in the paper measures relative values of polarisation of GFP fluorescence, the method does not measure the absolute strength of polarisation of the GFP fluorescence. The paper does not address or refer to the absolute strength of the polarisation itself, and furthermore does not address or refer to the strength of the polarisation of background auto-fluorescence. Thus, there is nothing in this paper to indicate or suggest that GFP fluorescence and background auto-fluorescence have significantly different strengths of polarisation, or to indicate or suggest that a polarisation measurement may be used to distinguish between GFP fluorescence and background auto-fluorescence.

The inventors are aware of a paper that mentions steady-state fluorescence anisotropy of GFP [K. D. Niswender, S. M. Blackman, L. Rohde, M. A. Magnuson, D. W. Piston. Quantitative imaging of green fluorescent protein in cultured cells: comparison of microscopic techniques, use in fusion proteins and detection limits. *Journal of Microscopy*, 1995, 180, 109]. This paper mentions that GFP fused with glutathione-S-transferase shows a fluorescence anisotropy of 0.29 and 0.34 when excited with light at 395 and 490 nm respectively. The paper mentions the different anisotropy values to suggest that different excited states and decay pathways may be involved depending on the wavelength of excitation. It is suggested that this may explain why photobleaching rates appear to be dependent on excitation wavelength. The paper does not address or refer to the strength of the polarisation of the GFP fluorescence, and furthermore does not address or refer to the strength of the polarisation of background auto-fluorescence. There is nothing in this paper to indicate or suggest that GFP fluorescence and auto-fluorescence have significantly different strengths of polarisation, or to indicate or suggest that a polarisation measurement may be used to distinguish between GFP fluorescence and auto-fluorescence. This is despite the fact that the paper is addressed towards the use of optical methods to combat auto-fluorescence.

The method according to the first aspect of the invention may be used in conjunction with any instrumentation, whether specially constructed for fluorescence polarisation measurement or adapted by the insertion of polarising filters. The method may be applied to flow through instrumentation (as described in detail below) or used with a conventional fluorimeter, a microscope, or a simple camera or CCD detector with a polarising filter placed between the illuminated sample and detector. The method may be used for the bulk analysis of solutions, or for visualisation applications of cells and organisms.

The method according to the first aspect of the invention is advantageous when compared to the prior art for several reasons. The method does not require expensive optimised filter sets, but instead uses inexpensive, easily modified polarising filters, and standard wider band filters. The method does not require complex and expensive instrumentation, as is required for two photon excitation spectroscopy, or for time resolved fluorescent spectroscopy. Where purification of a sample is carried out, as described above, the invention may allow a simpler, faster, less expensive purification method to be used, resulting in a 'dirtier' sample from which GFP fluorescence may be detected.

In some applications of the first aspect of the invention it may be preferable to make a measurement of 'brightness', rather than to simply measure fluorescence intensity. For example, GFP in yeast cells may be measured using the invention. Yeast cells will grow throughout the duration of an experiment, and a form of normalisation is required to convert the fluorescence detected during the experiment to a "brightness per cell" measurement. The brightness is calculated as: brightness=$(I_{\parallel}-I_{\perp})$/Cell density measurement, where cell density is quantified by either a turbidimetric or nephelometric method, or any other suitable cell counting method.

WO 98/44149 discloses methods of detecting the presence of an agent that causes or potentiates DNA damage, which involves subjecting cells to a putative DNA damaging agent and monitoring the expression of a light emitting reporter protein, such as GFP, from the cells.

WO 98/44149 further discloses recombinant DNA molecules comprising a regulatory element, which activates gene expression in response to DNA damage, that is operatively linked to a DNA sequence that encodes GFP or a derivative thereof. It also discloses recombinant vectors containing such DNA molecules. Each of these molecules and vectors may be used to transform cells (e.g. yeast) and may be used according to the DNA detecting method described in WO 98/44149.

The inventors have found that the methods described in WO 98/44149 (which are incorporated herein by reference) may be adapted, and improved, such that light emitted from GFP in response to DNA damage may be distinguished from auto-fluorescent molecules according to the method of the present invention. This allows the detection of DNA damage with improved sensitivity. Thus according to a preferred embodiment of the present invention light emitted from GFP contained within or derived from host cells genetically engineered to express GFP (e.g. yeast genetically engineered to express GFP in response to DNA damage) may be distinguished from auto-fluorescence and thereby provide an improved manner of monitoring for GFP expressed from said cells.

The method according to the first aspect of the invention is therefore useful for improving the sensitivity of various biological assays that rely upon light emitted from GFP as a marker. It will be appreciated that recombinant DNA technology may be utilised to allow expression of GFP to be regulated by many different signals (e.g. DNA damage) and therefore the utility of GFP as a marker, and thereby the benefits of the method of the present invention will be wide ranging.

The method according to the first aspect of the invention may also be applied to apparatus that produces an image, wherein two images taken of fluorescent light having two different polarisations are digitally or otherwise subtracted. Areas of the image arising from auto-fluorescence should be reduced in intensity to a much greater extent than those areas showing GFP fluorescence.

According to a second aspect of the invention there is provided an apparatus for distinguishing between fluorescent light emitted by green fluorescent protein and fluorescent light emitted by auto-fluorescent molecules, the apparatus comprising:

illumination means for illuminating a sample containing green fluorescent protein and auto-fluorescent molecules using plane-polarised light;

detector means for detecting the intensity of fluorescent light that is emitted with a first polarisation from the sample;

detector means for detecting the intensity of fluorescent light that is emitted with a second polarisation from the sample; and subtraction means for subtracting a first of said detected intensities from a second of said detected intensities to provide a difference signal.

BRIEF DESCRIPTION OF THE DRAWINGS

A specific embodiment of the invention will now be described, by way of example only, with reference to the accompanying figures, in which.

DETAILED DESCRIPTION OF THE PREFERRED EMBODIMENTS

The described embodiment of the invention is a flow-through apparatus dedicated to the measurement of fluorescence polarisation of GFP, using two carefully matched photodetectors, in conjunction with two polarising filters in fixed orientations to measure the intensity of fluorescence perpendicularly polarised with respect to a laser light source ($I_⊥$) and the intensity of fluorescence aligned parallel to the laser light source ($I_‖$). The apparatus also incorporates a third photodetector for on-line absorption measurements to allow estimation of yeast cell concentrations.

The effective discrimination between GFP fluorescence and auto-fluorescence in a sample is demonstrated by two methods using the described embodiment; a flow injection and a continuous flow approach, for GFP both in free solution and within intact, living yeast cells.

The description illustrates how fluorescence polarisation may be used to enhance the detection of GFP expressed by genetically modified yeast cells in the presence of cellular auto-fluorescence.

The particular GFP derivative used in the described embodiment of the invention is "yeast-Enhanced GFP" (yEGFP) in which two types of modification have been carried out: codon optimisation for yeasts and amino acid substitutions shown to increase the fluorophore efficiency, most critically serine 65 to threonine [B. P. Cormack, G. Bertram, M. Egerton, N. A. R. Gow, S. Falkow and A. J. P. Brown, *Microbiology*, 1997, 143, 303]. These modifications result in a fluorophore that is excited at 490 nm and emits at approximately 517 nm Three strains of the brewers yeast *Saccharomyces cerevisiae* were used; out low auto-fluorescent optimised strain FF18984, and two further strains which demonstrated high auto-fluorescence, FY73 and YJL047c. Both wild-type and genetically modified (GM) variants of each strain were used. The strains were genetically modified by fusing the promoter of the gene responsible for the induction of a native protein, Rad54, with the (yEGFP) gene. The details of this modification have been previously reported [R. M. Walmsley, N. Billinton and W.-D. Heyer, *Yeast*, 1997, 13, 1535; N. Billinton, M. G. Barker, C. E. Michael, A. W. Knight, N. J. Goddard, P. R. Fielden and R. M. Walmsley, *Biosens. Bioelectron.*, 1998, 13, 831]. Synthesis of the Rad54, protein is known to be up-regulated whenever yeast DNA repair mechanisms are activated in response to DNA damage, for example upon exposure to a genotoxic agent or ionizing radiation. The embodiment of the invention is used to show how by exposing the genetically modified cells to a low concentration (typically 0.005% v/v) of methyl methanesulfonate (MMS) in the culture medium, GFP expression and accumulation in the cells is observed by a marked increase in green fluorescence. MMS (99%, Sigma-Aldrich Gillingham, UK) is a known genotoxic alkylating agent.

Cultures of whole yeast cells used in this work were prepared as follows. A small aliquot from a freshly prepared culture of the cells was inoculated into 50 ml. of medium in a conical flask, to give a starting cell density of approximately 0.1 $OD_{488}$. ($OD_{488}$=optical density measured using a 1 cm path length and illumination at 488 nm) MMS was added to the flask immediately after inoculation if required. The culture was then incubated at 28° C., with orbital shaking, for between 16 and 24 hours, reaching a final cell density of between 1 and 3 $OD_{488}$, depending on the (MMS) concentration used. For whole cell measurements the cultures were used without further treatment, except for dilution of the most dense cultures with fresh medium (without glucose) just prior to use.

GFP extracts were prepared from the MMS induced cells according to the procedure previously described by Walmsley et al. [see above] and Billinton, et al. [see above]. A 50 ml culture produced on average 0.5 ml of protein extract. The buffer used was at pH 7.0 and consisted of 0.02 mol $l^{-1}$ tris(hydroxymethyl) methylamine - hydrogen chloride (>99%, Roche Molecular Biochemicals), 0.1 mol $l^{-1}$sodium chloride (GPR grade, BDH Ltd., Poole, Dorset, UK), $1\times10^{-3}$ mol $l^{-1}$ ethylenediamine-tetraacetic acid (GPR grade, BDH Ltd.), and $1\times10^{-3}$ mol $l^{-1}$ phenylmethanesulfonyl fluoride (>99%, Sigma-Aldrich).

"F1", a well defined minimal medium, was used for culturing the yeast cells investigated in this work [R. M. Walmsley, D. J. C. Gardner and S. G. Oliver, *Mol. Gen. Genet.*, 1983, 192, 361]. This medium was chosen as it exhibited very low fluorescence at the wavelengths concerned. Two further media were investigated for their autofluorescence and fluorescence polarisation properties, and are discussed in detail later.

Fluorescence standards of fluorescein sodium salt (90%), acridine orange (>98%), 8-hydroxypyrene- 1,3,6-trisulfonic acid trisodium salt (HPTSA)(>95%), and rhodamine 110 chloride (>99%) were obtained from Sigma-Aldrich. Where stated the fluorophores were used in a phosphate buffer, which comprised of 0.02 mol $l^{-1}$ sodium dihydrogen orthophosphate (AnalaR grade, BDH Ltd.) adjusted to pH 8.25 with sodium hydroxide (Volumetric Standard, 0.969 N solution in water, Sigma-Aldrich).

A paper written by the inventors and published in March 1999 (Fluorescence polarisation of green fluorescent protein (GFP). A strategy for improved wavelength discrimination for GFP determinations; A. W. Knight, N. J. Goddard, P. R. Fielden, M. G. Barker, N. Billinton and R. M. Walmsley, Anal Commun., 1999, 36, 113–117) describes using an instrument which consists of a single photodetector and a rotating polarising filter, arranged at right angles to the polarised laser beam passing through an optical cell. The filter is manually rotated between parallel and perpendicular fluorescence measurements. This paper is herein incorporated by reference.

Figure 1:
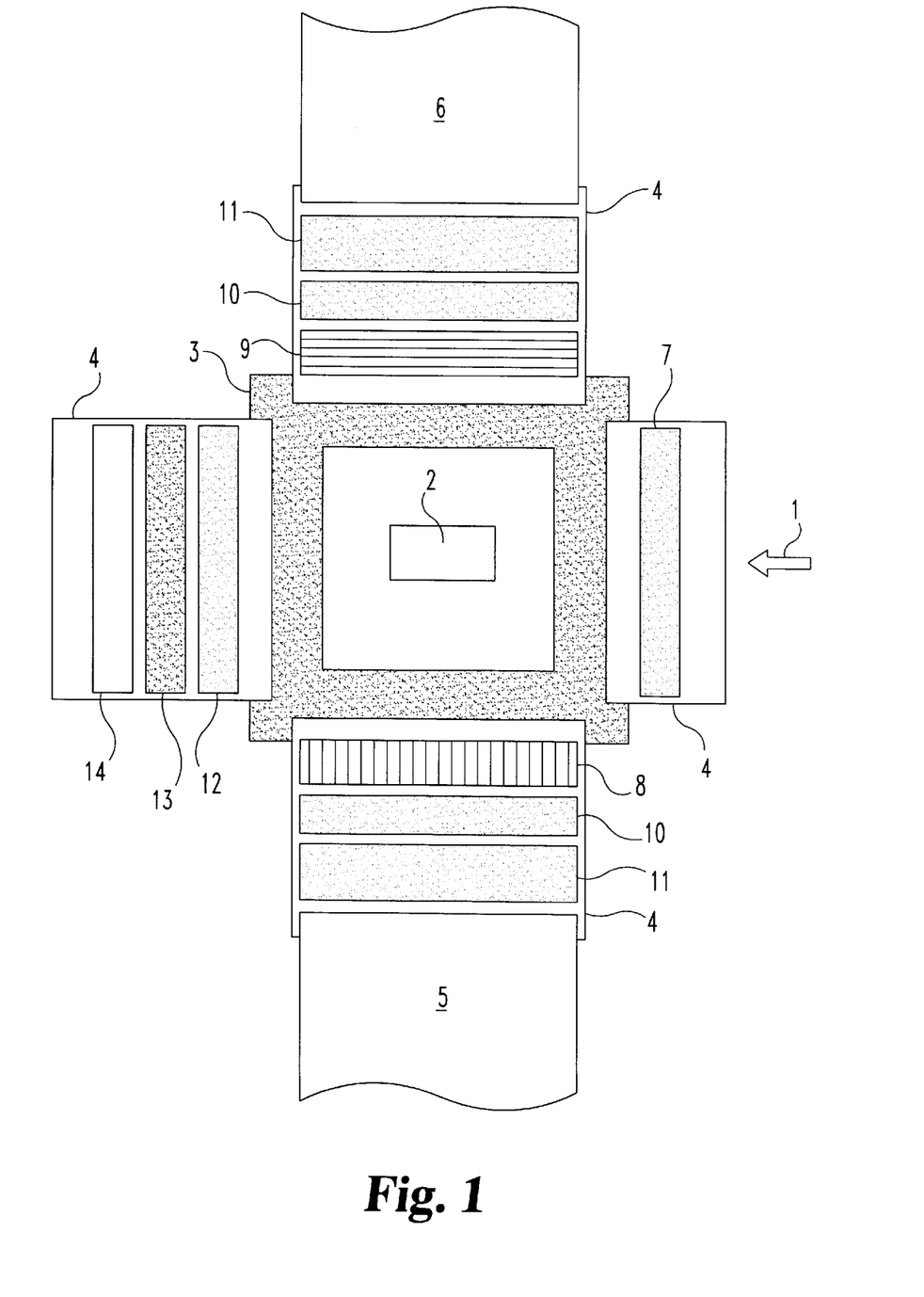
FIG. 1 is a schematic illustration of a fluorescence measurement apparatus according to the second aspect of the invention.

The embodiment of the invention illustrated in FIG. 1 allows simultaneous measurements of both parallel and perpendicularly polarised fluorescence, and in addition the absorbance of the sample as it passes through an optical flow cell.

An air cooled argon ion laser (162LGL, LG Laser Graphics GmbH, Dieburg, Germany), provided a 488 nm excitation light beam of 5 mW after filtering ($TEM_{00}$>95%, beam diameter 0.67±0.05 mm). The light beam is represented by the arrow 1 in FIG. 1. The light beam 1 was plane polarised (>100:1). A four window quartz fluorescence flow cell 2 with an internal volume of 132 μl, specially constructed by Hellma Ltd, Southend-on-Sea, UK was housed in a cubic black plastic mounting block 3 (30×30×30 mm). The mounting block 3 was built at the University of Manchester Institute of Science and Technology. Four internally threaded optical mounting tubes 4, 19 mm in diameter, were fixed to the mounting block 3, and were used to hold the various filters in place. All filters and mounts were purchased from Comar Instruments, Cambridge, UK. The polarisation of the light beam 1 was perpendicular to the base of the mounting block 3.

Miniature photomultiplier tubes 5, 6 (PMTs) supplied by Hamamatsu Photonics Ltd., Enfield, UK, were used for fluorescence light detection. The PMTs 5, 6 were supplied within compact modules (H5784) which housed the PMT, high voltage power supply and additional amplifying circuit, such that they could be run from a conventional ±12 V power supply.

A 488 nm interference filter 7, (3 nm half bandwidth), was used to filter the excitation light beam 1. At right angles to the beam path, two polarising filters 8, 9 were securely mounted. One filter 8, 9 was rotated through 90° with respect to the other, such that one PMT 5 recorded the fluorescence intensity emitted polarised parallel with respect to the excitation beam ($I_{\parallel}$), and the other PMT 6 recorded that emitted polarised perpendicular with respect to the excitation beam ($I_{\perp}$). The polarising filters 8, 9 were 16 mm diameter disks, cut by hand from a polaroid sheet (Grade HN38) laminated in cellulose acetate butyrate (thickness=0.8 mm). Additional filters were optimised and used in conjunction with the polarising filters to allow the laser-induced GFP fluorescence at 517 nm to be measured, whilst rejecting the high intensity laser light at 488 nm scattered towards the detector by yeast cells suspended in the stream of liquid passing through the flow cell. These filters consisted of 515 nm interference filters 10 (10 nm half bandwidth), and 515 mm short wave cut-off filters 11 fabricated from three layers of orange Schott Glass (OG 515, thickness=3 mm), each layer comprising of a 16 mm diameter disk cut from the supplied material using a diamond cutter. 515 nm filters were used as they were close to the GFP emission maximum and were commercially available.

The apparatus shown in FIG. 1 was also used to carry out absorbance measurements. A second 488 nm interference filter 12 (3 nm half bandwidth), and a neutral density filter 13 (OD=3 at 488 nm) were placed in front of a silicon photodiode (SPD) detector 14 (IPL10530DAL, RS Components Ltd., Corby. UK). The 488 nm interference filter 12 rejected fluorescence emissions, whilst the neutral density filter 13 reduced the power of the laser beam 1 to a level suitable for the SPD detector 14. The SPD detector 14 was provided in a package which also contained a lens (not shown) to focus the laser beam onto the detector 14 (which comprised a 1.75 $mm^2$ detection chip).

Figure 2:
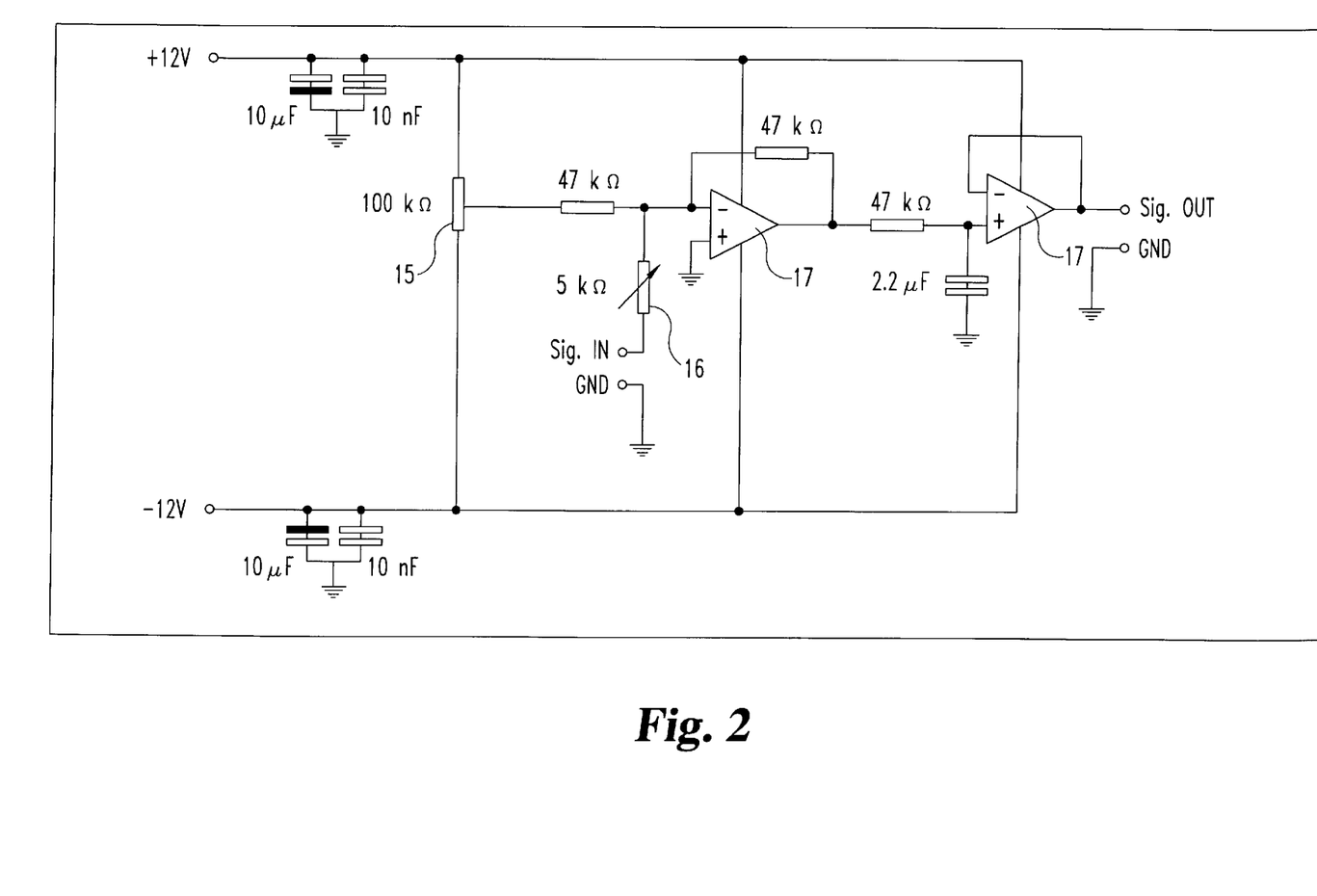
FIG. 2 is a circuit diagram of an operational amplifier circuit comprising part of the apparatus illustrated in FIG. 1.

The voltage signals from the PMT 5, 6 and SPD 14 detectors were processed by a simple op-amp circuit built at the University of Manchester Institute of Science and Technology. The op-amp circuit comprised, in part, of three sub units, one of which is shown in FIG. 2. One sub-unit was used for each light detector. The op-amp circuit allowed an incoming signal to be offset by addition of a positive or negative voltage selected by a 100 kΩ variable resistor 15, such that a "dark" or "blank" baseline signal level can be established. The degree of amplification of incoming signals is adjustable using a 5 kΩ variable resistor 16, thus allowing the sensitivity of the two PMT detectors shown in FIG. 1 to be equalised. The signals are smoothed by the use of a simple low-pass filter, and an additional voltage-follower further isolates the photo-detector from the recording device. To save circuit board space, quad op-amps 17 were used (AD713JN) which were obtained, along with all other electrical components, from RS Components Ltd.

Data acquisition and subsequent manipulation was carried out in real time using a personal computer (not shown) connected to the op-amp circuit via a 10 bit analogue to digital converter (ADC-11, Pico Technology Ltd., Cambridge, UK) and associated software. The data collection rate was 1 sample $s^{-1}$, each sample being an average of 1000 readings taken during the sample interval.

As mentioned above, each PMT was provided as part of a module which included an amplifying circuit. The sensitivity of the amplifying circuit built into each PMT module was controlled by means of an externally applied control voltage in the range 0 to 1.0 V. The control voltage was selected by means of a digital potentiometer using a reference voltage of +1.2 V, supplied by the module itself, and applied to both PMTs simultaneously. This provided a means by which to scale the fluorescent signals for any particular experiment, such that the full voltage range of the ADC (0 to +2.5 V) would be utilised, giving maximum resolution.

The optical apparatus shown in FIG. 1, the op-amp circuit, and its ±12 V power supply were housed inside a light-tight box (not illustrated) with a shuttered aperture attached to the head of the laser. For measurement of large volumes of sample (>2 ml), a sample was circulated continuously through the fluorescence flow cell 2 at a flow rate of 1.0 to 1.5 ml min$^{-1}$ whilst replicate readings of $I_{//}$ and $I_\perp$ were obtained. Alternatively, and especially for small sample volumes (<2 ml), a flow-injection approach was adopted. Injections of 70 μl aliquots of the sample were made into a suitable carrier stream flowing through the fluorescence flow cell 2 by means of a rotary injection valve (Type 50, Rheodyne Inc., Cotati, Calif., USA). The resulting flow-injection peaks were integrated using Visual Basic software written at the University of Manchester Institute of Science and Technology. The internal liquid volume of the apparatus including all tubing was approximately 1 ml.

A standard commercial fluorescence spectrometer (LS50-B, Perkin Elmer) was used to carry out conventional measurements of fluorescence, scattered light intensity and for obtaining excitation and emission spectra, with a 1 cm path length acrylic cuvette (not shown). A yellow Schott glass filter (not shown) (YG495, thickness=3 mm) was placed within the sample chamber directly in front of the window of a PMT, in order to block excitation light scattered towards the PMT by yeast cells suspended in the cuvette. For fluorescence measurements the excitation and emission wavelengths were 490 and 520 nm respectively. For light scattering nephelometric measurements, the excitation and emission wavelengths were both 600 nm. Light intensity was recorded in arbitrary units produced directly by the instrument software.

In order to accurately quantify $I_{//}$ versus $I_\perp$ and thus obtain fluorescence polarisation measurements, the sensitivity of the PMTs 5, 6 and associated circuitry needed to be balanced, such that each PMT 5, 6 responded identically to increasing fluorescence light intensity. This was achieved by fine adjustment of the variable resistors 16 in the circuit shown in FIG. 2, whilst a solution of a suitable fluorophore was pumped through the fluorescence flow cell 2. This adjustment needed to be performed with the polarising filters 8, 9 in place, since dismantling the instrument optics to insert the polarising filters 8, 9 after the sensitivity adjustment invariably led to slight errors in the alignment of filters, and thus a change in the apparent PMT 5, 6 sensitivity. Hence, a fluorophore needed to be selected which had very similar spectroscopic properties to GFP, but which exhibited extremely low, or no, fluorescence polarisation when excited by plane polarised light. Thus the sensitivity of the PMTs 5, 6 could be balanced with all the filters 8–11 in place, such that with the fluorophore passing through the flow cell 2, $I_{//}=I_\perp$ and P=0, in effect establishing a baseline.

Four fluorophores were chosen, which were close spectroscopic mimics of GFP. These were fluorescein, rhodamine 110, acridine orange and HPTSA. Using the commercial fluorescence spectrometer (not shown), the fluorescence excitation and emission spectra for each fluorophore and for GFP were obtained. This gave the wavelength maxima shown in Table 1, to the nearest 0.5 nm. The GFP sample was a cellular extract diluted 10 fold with distilled water. The emission spectra of fluorescein and HPTSA closely overlapped that of GFP, whereas those of rhodamine 110 and acridine orange were slightly red-shifted with respect to GFP. The excitation maxima of all the compounds tested closely matched that of GFP except for that of HPTSA at 455 nm. However, since HPTSA exhibits a high fluorescence yield and there is sufficient overlap of the excitation spectra of HPTSA and GFP to allow excitation of HPTSA at 488 nm, this fluorophore could be used as a GFP mimic in the system. HPTSA needed to be used at 20 times the concentration of fluorescein to obtain the same magnitude fluorescence signal.

To measure the fluorescence polarisation ratio (P) of the fluorophores, two polarising filters (not shown) (Grade HN38 polaroid sheet, laminated in rigid acrylic, thickness= 3.4 mm) were inserted within the housing 3, one either side of the sample cuvette (Which was used in place of the flow cell 2). By manually rotating the second polarising filter placed between the cuvette and fluorimeter PMT, through 90° measurements of $I_{//}$ and $I_\perp$ could be readily obtained. Table 1 shows the average P values obtained from 20 replicate readings for each fluorophore along with their fluorescence lifetimes as quoted in the literature. The results obtained indicated that HPTSA shows the lowest fluorescence polarisation of the fluorophores tested with less than 0.5% difference between $I_{//}$ and $I_\perp$. Fluorescein and rhodamine 110 gave small but significant P values of similar magnitude, as might be expected due to their similar structures. Acridine orange consistently produced a higher P value of 0.0141. HPTSA was therefore chosen to balance the sensitivities of the two PMTs. GFP in the cellular extract gave a predictably high P value of 0.398. This is slightly higher than the result previously reported [A. W. Knight, N. J. Goddard, P. R. Fielden, M. G. Barker, N. Billinton and R. M. Walmsley. *Anal. Commun.*, 1999, 36, 113.]. The reason for this is the higher concentration of GFP in this extract compared to other cellular auto-fluorescent species, which reflects further optimisation of the GFP induction, expression and extraction procedures. By measuring the fluorescence of an extract of a wild type culture grown under the same media conditions, and correcting for total protein concentration ($OD_{280}$), it was predicted that the cellular auto-fluorescence would contribute approximately just 3% of the total fluorescence signal in this particular GFP extract. Hence 0.398 will be very close to the true value of P that would be obtained from a solution of pure GFP Polarisation ratio can be seen to generally increase with decreasing fluorescence lifetime in Table 1. This may be expected since the longer the fluorescence lifetime, the greater the time available between excitation and emission for the molecule to become randomly orientated in solution, and thus produce an isotropic fluorescence emission. Although GFP exhibits the shortest fluorescence lifetime of 2.6 to 2.9 ns, it is likely that its marked fluorescence polarisation and high P value is more attributable to its large size (27 kDa), and hence slow rotation rate. Swaminathan et al. [R. Swaminathan, C. P. Hoang and A. S. Verkman, *Biophys. J.*, 1997, 72, 1900] determined the rotational correlation time of GFP (S65T derivative) to be 20 ns in aqueous solution and 36 ns in cell cytoplasm. Hence, the fluorescence lifetime of GFP was observed to be considerably less that its rotational correlation time. In comparison fluorescein had a rotational correlation time of 120 ps, approximately 40 times shorter than its fluorescent lifetime.

At the maximum sensitivity setting afforded by a digital potentiometer, the signals from both PMTs were equalised with a solution of $4 \times 10^{-8}$ mol $1^{-1}$ HPTSA in phosphate buffer, passing through the flow cell at 1.0 ml min$^{-1}$.

To determine the absolute sensitivity of the apparatus, a calibration was performed by measuring $I_{//}$ for a range of fluorescein standards and a blank. On the most sensitive settings a calibration could be performed over the concentration range 1 to $20 \times 10^{-10}$ mol $1^{-1}$, which gave a signal range of 0 to +2.0 V. A sensitivity of 0.096 V/$10^{-10}$ mol $1^{-1}$ fluorescein and a limit of detection of $2 \times 10^{-11}$ mol $1^{-1}$ (equivalent to 5 times the standard deviation of the blank) were achieved. It should be noted that the polarising filters used have a transmission of 38%, and in the absence of the polarising filters fluorescein can be readily detected in the pmol $1^{-1}$ range, using the same optical set-up.

Figure 3:
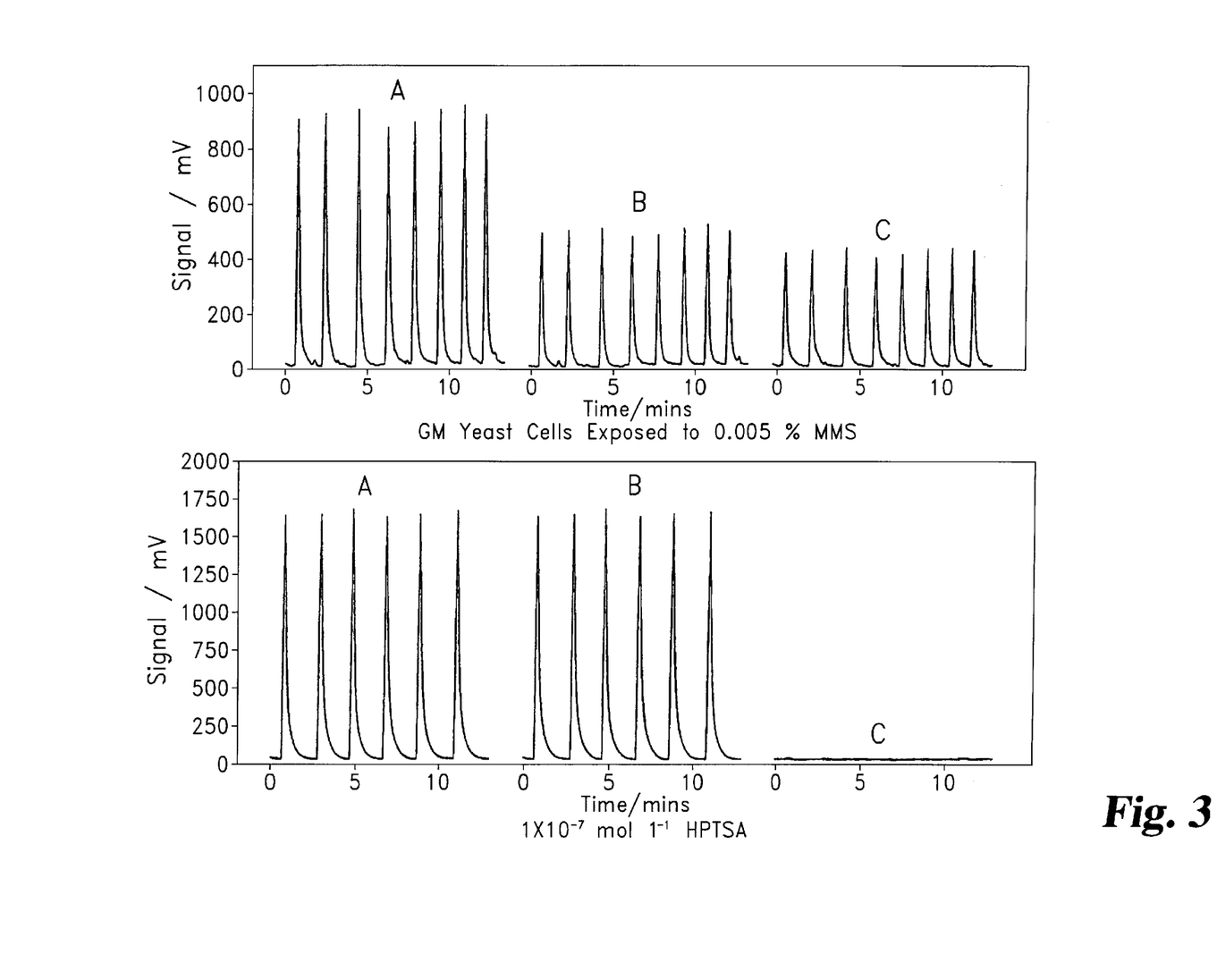
FIG. 3 is a graph showing fluorescence emitted by green fluorescent protein expressed in genetically modified yeast cells, and auto-fluorescence emitted by 8-hydroxypyrene-1, 3,6-trisulfonic acid trisodium salt, measured using the apparatus illustrated in FIG. 1.

FIG. 3 shows the typical response from the instrument when used with flow-injection analysis. A culture of GM-FF18984 yeast cells was inoculated into F1 media containing 0.005 % MMS and incubated at 28° C. for 18 hours. The final culture was diluted 50:50 with fresh F1 media, containing no glucose, to give a yeast cell suspension of 0.58 OD$_{488}$. 70 ml aliquots of the culture were injected into a carrier stream of F1 media, again without glucose, flowing at a rate of 1.5 ml min$^{-1}$. In FIG. 3, A and B represent the response from the PMTs measuring parallel and perpendicularly orientated fluorescence respectively. The analytical signal is the difference between these responses ($I_{//}$–$I_{\perp}$), recorded in real time and shown in trace C. Using the peak areas for each injection, the average fluorescence polarisation ratio was found to be 0.310 for GFP within whole yeast cells, which results in an analytical signal approximately 50% as great as $I_{//}$ alone. The P value is slightly lower than that obtained for the GFP extracted from cells due to the additional auto-fluorescence from the yeast cells as discussed later. The signal however, is still large and well resolved.

The potential of using fluorescence polarisation is clearly demonstrated by the response obtained for HPTSA, as shown in FIG. 3. 70 μl aliquots Of $1 \times 10^{-7}$ mol $1^{-1}$ HPTSA were injected into a carrier stream of phosphate buffer flowing at a rate of 1.0 ml min$^{-1}$. Large responses are recorded by both PMTs, however as $I_{//} \approx I_{\perp}$, and P≈0, the difference signal ($I_{\perp}$–$I_{//}$) is close to zero, resulting in a flat baseline being recorded as the analytical signal. The same response was obtained for fluorescein under similar conditions. Hence the apparatus clearly discriminates the polarised fluorescence of GFP from the isotropic fluorescence of smaller fluorophores, occurring at the same wavelength.

The average relative standard deviation in peak areas from injections of yeast cell suspensions was <3%, and from the fluorophores in solution <1%. The lower reproducibility for yeast cultures was attributed to effects resulting from inhomogeneous mixing as the denser yeast culture is injected into the F1 media carrier stream flowing into the optical cell. In addition increased noise was observed in the signals due to variations in the level of induction of GFP, and hence brightness, of individual cells. The former effect was minimised by careful selection of the carrier stream, diluting culture densities to less than 1 OD$_{488}$ and adjustments to the flow rate.

It was noted that a higher flow rates, >1.5 ml min$^{-1}$, a small negative peak resulted for injections of HPTSA and fluorescein. This was due to a slightly slower response of the PMT and associated circuitry measuring the $I_{//}$ signal compared to that measuring the $I_{\perp}$ signal, during the sharply rising front edge of the flow-injection peak. This problem could be resolved either by making the detection circuits faster by lowering the value of a smoothing capacitor of the sub-circuit shown in FIG. 2, or by using closely matched precision components. However, the use of flow rates less than or equal to 1.5 ml min$^{-1}$ removed this effect.

For continuous flow analysis a sample was pumped through the instrument at a flow rate of 1.0 to 1.5 ml min$^{-1}$ whilst replicate readings of $I_{//}$ and $I_{\perp}$ were accumulated. Typically 20 replicate readings were obtained for each sample, with a relative standard deviation of <1.5% for whole cells expressing GFP.

Figure 4:
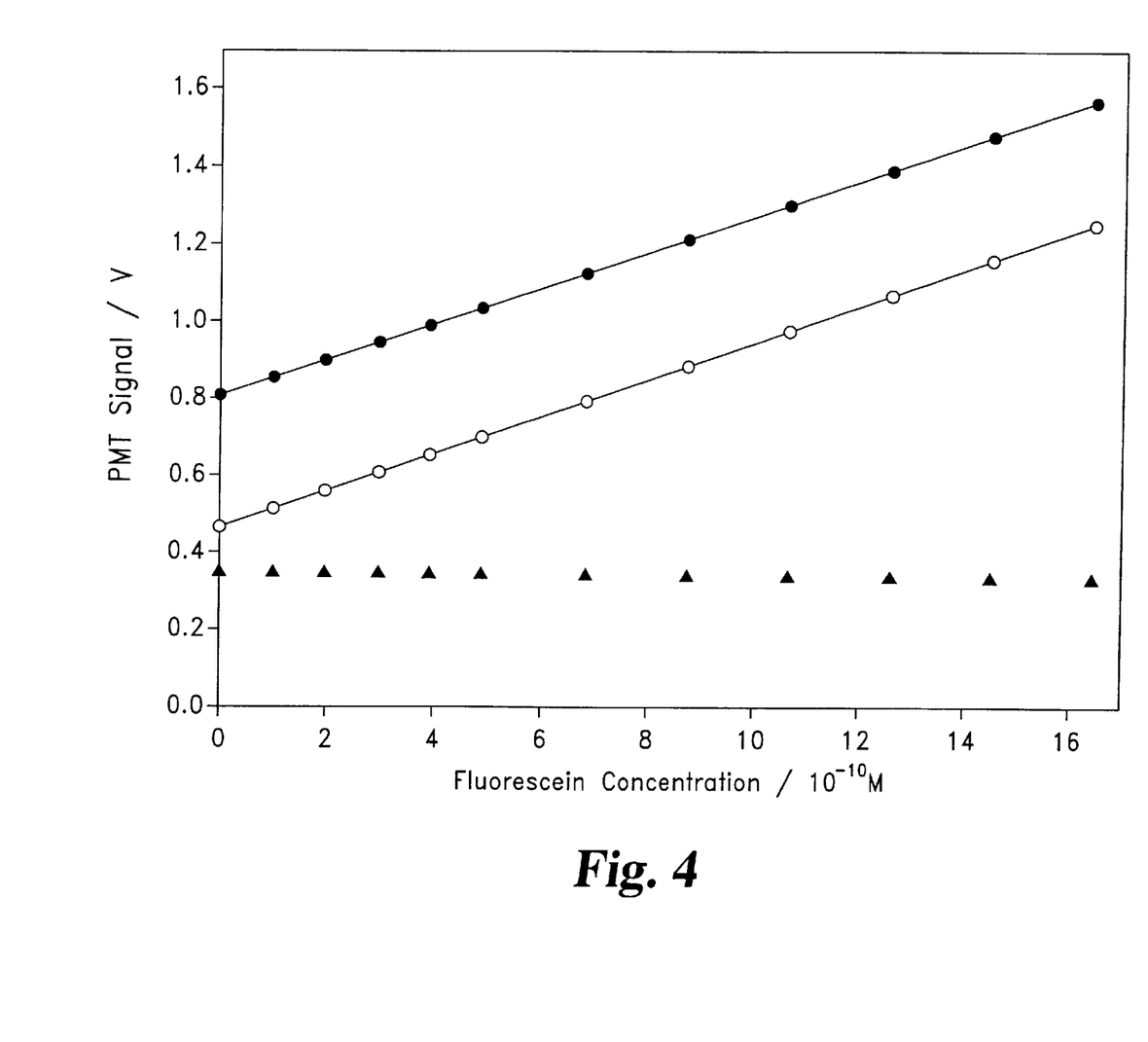
FIG. 4 is a graph showing fluorescence emitted by green fluorescent protein expressed in genetically modified yeast cells in the presence of fluorescein, measured using the apparatus illustrated in FIG. 1.

To demonstrate the effectiveness of the fluorescence polarisation approach in a continuous flow method, an experiment was carried out with whole cells similar to that previously performed using extracts of GFP [A. W. Knight, N. J. Goddard, P. R. Fielden, M. G. Barker, N. Billinton and R. M. Walmsley, *Anal. Commun.*, 1999, 36, 113]. A series of samples were made up each containing 0.3 OD$_{488}$ GM-FF18984 yeast cells from a stock culture grown overnight in the presence of 0.005% MMS, to which increasing concentrations of fluorescein were added, ranging from 0 to $16.5 \times 10^{-10}$ mol $1^{-1}$. The results are shown in FIG. 4. In FIG. 4, filled in circles represent fluorescence detected with a polarisation parallel to an excitation beam ($I_{//}$), hollow circles represent fluorescence detected with a polarisation perpendicular to the excitation beam ($I_{\perp}$), and filled in triangles represent the difference between the detected fluorescence signals =($I_{//}$–$I_{\perp}$). As the fluorescein concentration increases, the signals for $I_{//}$ and $I_{\perp}$ increase linearly, such that at the highest fluorescein concentration tested the $I_{//}$ signal is twice as intense as the GFP alone. However, since for fluorescein $I_{//} \approx I_{\perp}$, by taking the signal for GFP as the difference between these measurements, the increase in fluorescence caused by the addition of fluorescein to the yeast cell culture could be effectively removed from the measurement. The measurements for GFP ranged from 0.345 to 0.327 V with an average of 0.336 V and a relative standard deviation of 1.97% (n=12).

In order to correct for variations in cell density between cultures, the fluorescence measurements were normalised by quoting a "brightness", essentially the fluorescence in arbitrary units per cell. Fluorescence is corrected for cell density because the yeast cells are growing through the duration of the experiment, thereby necessitating normalisation of the total fluorescence measurement to produce a "brightness per cell". The brightness is calculated as: The fluorescence signal mathematically divided by the cell density signal. The cell density signal may be determined from measurements of absorbance (turbidimetric method), or from measurement of the intensity of scattered light (nephelometric method).

The calculation of brightness differed depending upon whether the fluorescence was measured using the method according to the invention, or whether the fluorescence was measured in the conventional manner.

Where the fluorescence was measured in the conventional manner, using the LS50-B spectrometer, culture density was quantified by nephelometry. This conventional measurement will be referred to hereafter as the "normal fluorescence" method. For this normal fluorescence method, brightness ($B_{nf}$) was defined as the fluorescence intensity at 520 nm (excitation wavelength=490 nm), divided by the scattered light intensity at 600nm. Using a series of yeast cell cultures in the range 0 to 1 OD, the scattered light intensity was found to vary linearly with $OD_{600}$ according to the relationship; $OD_{600}=0.0023\times$scatter intensity, (correlation coefficient=0.99917, n=20).

When the fluorescence was measured using the method according to the invention, culture density was quantified on-line using a turbidimetric method. The SPD (14 in FIG. 1) measured the drop in the intensity of the laser beam as it passed through the optical cell, due to scattering and absorption of the light by the suspension of yeast cells. The method of measuring fluorescence according to the invention is referred to hereafter as the "fluorescence polarisation" method. For the fluorescence polarisation method, brightness ($B_{fp}$) was defined as, the difference signal ($I_{||}-I_{|}$), divided by the SPD signal. Using a series of yeast cell cultures in the range 0 to 2 OD, the SPD signal (V) was found to vary with $OD_{488}$ according to the quadratic relationship; $OD_{488}=(1.31\times$SPD signal$)+(0.253\times$SPD signal$^2$), (correlation coefficient=0.99999, n=15).

With the wild-type yeast cells, since the optical density arises primarily from the scattering of light passing through the culture as opposed to absorption, there is no significant difference between OD measurements made at 488 nm and the more commonly used 600 nm. In each case the measured OD relates linearly to the actual yeast cell concentration up to an OD of about 0.6, and is generally a reliable indicator of cell concentration up to an OD of 1.0. Above an OD of 1.0 this measurement underestimates the number of cells, as the relationship between cell concentration and OD deviates from linearity. Hence in the calibration equations given, for dense cultures with an OD greater than 0.6, $OD_{488}$ and $OD_{600}$ used are those that would be obtained by diluting back into the linear range, and scaling up the OD measurement obtained by the dilution factor. In this way OD measurements can be used to accurately measure culture density.

The measurements of GFP in both whole yeast cells and protein extracts are unavoidably made in the presence of cellular auto-fluorescence. An investigation was carried out to examine the intensity of this auto-fluorescence, its spectroscopic properties, the extent of its fluorescence polarisation, and whether the application of fluorescence polarisation would enhance the measurement of GFP induction by MMS in its presence. Three yeast strains were selected from other related studies within our laboratory; FF18984, a strain selected empirically for low intrinsic auto-fluorescence and high GFP induction during DNA damage repair; FY73, a strain exhibiting generally higher auto-fluorescence; and YJL047c, a strain exhibiting high auto-fluorescence that was further increased after exposure of the cells to MMS. Table 2 shows the intensity of the auto-fluorescence in cultures of the various wild-type, un-modified yeast strains, grown with and without the presence of MMS. The commercial fluorescence spectrometer (LS50-B, Perkin Elmer) was used to obtain brightness values using the normal fluorescence method ($B_{nf}$). The brighter auto-fluorescence from FY73 and YJL047c is clearly demonstrated in Table 2, as is the additional induced fluorescence in YJL047c resulting from the presence of increasing concentrations of MMS.

Figure 5:
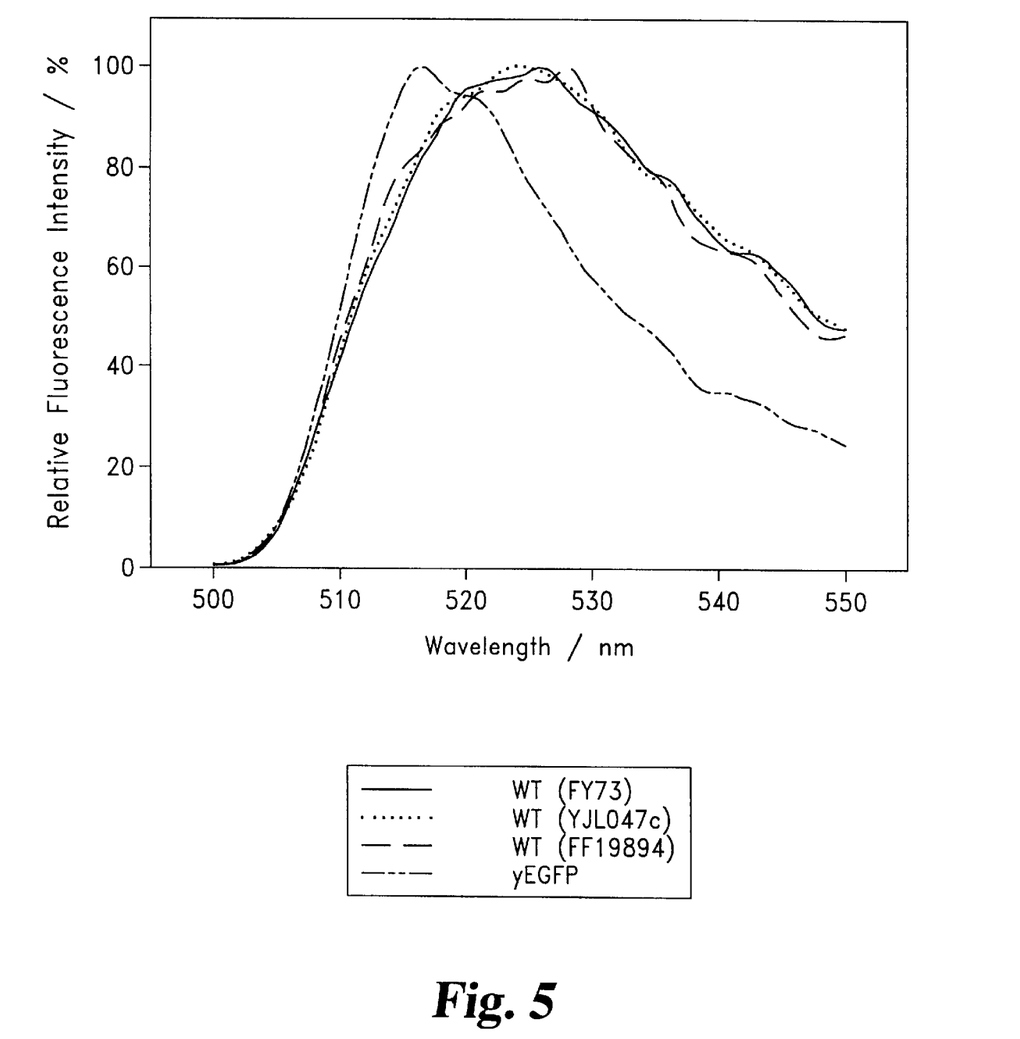
FIG. 5 is a graph showing auto-fluorescence spectra of various strains of wild-type yeast cells.

The fluorescence spectra of the three selected wild-type yeast strains upon excitation at 488 nm are shown in FIG. 5. A 495 nm Schott Glass cut-off filter was located in front of the commercial fluorescence spectrometer. This was routinely done to remove interference from excitation light scattered when measuring yeast cell suspensions, both during spectrometer measurements and fluorescence polarisation measurements. The spectra were found to be almost identical and thus the auto-fluorescence is thought to originate from the same species in each case. The exact source of the auto-fluorescence is still under investigation, however there are several likely candidates, including reduced nicotinamide nucleotides, oxidised flavins, age related pigments and oxidised aromatic amino acids such as tryptophan. FIG. 5 also shows the fluorescence spectrum of GFP (yEGFP variant). This was obtained by subtracting a spectrum of a cellular extract of the wild type FF18984 cells from the spectrum of GFP in a cellular extract of GM cells grown under the same media conditions, with both spectra corrected for their total protein concentration ($OD_{280}$). A clear peak at 517 nm is observed for GFP, however its spectrum is almost completely overlapped by that of the cellular auto-fluorescence inherent to all the strains, which takes the form of a broad peak with maxima in the range 524 to 528 nm.

The GFP measurement method according to the described embodiment will provide useful results provided that an interfering species emitting at the same wavelength as GFP produces fluorescence that is less polarised than that produced by the GFP, i.e. has a lower fluorescence polarisation ratio. When this is the case, when a difference measurement ($I_{||}-I_{|}$) is made, a greater proportion of the auto-fluorescence signal will be removed than the GFP signal. Hence, an increase in the "signal to background noise" ratio will result.

From the wild-type cultures examined the average polarisation ratios obtained for the FY73 and YJL047c strains were 0.044 and 0.043 respectively. The polarisation ratio observed for the less fluorescent FF18984 strain was consistently higher, with an average value of 0.079. Hence, one might speculate that the additional fluorescence of the FY73 and YJL047c strains may be due to smaller species with greater rotational rates. However, since the fluorescence spectra of the three strains were so similar, similar species in the FF18984 strain may be attached to, or be an intrinsic part of, larger proteins or other molecules. In each case the fluorescence polarisation ratios are significantly lower than that of GFP and hence the polarisation method should be effective in discriminating between GFP and this auto-fluorescence.

It is often useful to quantify the degree of genotoxic action of a test compound by the apparent "induction ratio" of GFP in the GM yeast cell culture. The induction ratio is defined as: the brightness of a GM yeast cell culture exposed to the test compound, divided by the brightness of a similar culture not exposed to the test compound. For accuracy the two test cultures, effectively a sample and control, are sub-cultured from the same source and grown up under identical media and temperature conditions. The brightness measurements of both cultures are taken at the same time, usually after the exposed culture has reached maximum GFP induction, about 10 to 12 hours after exposure.

Figure 6:
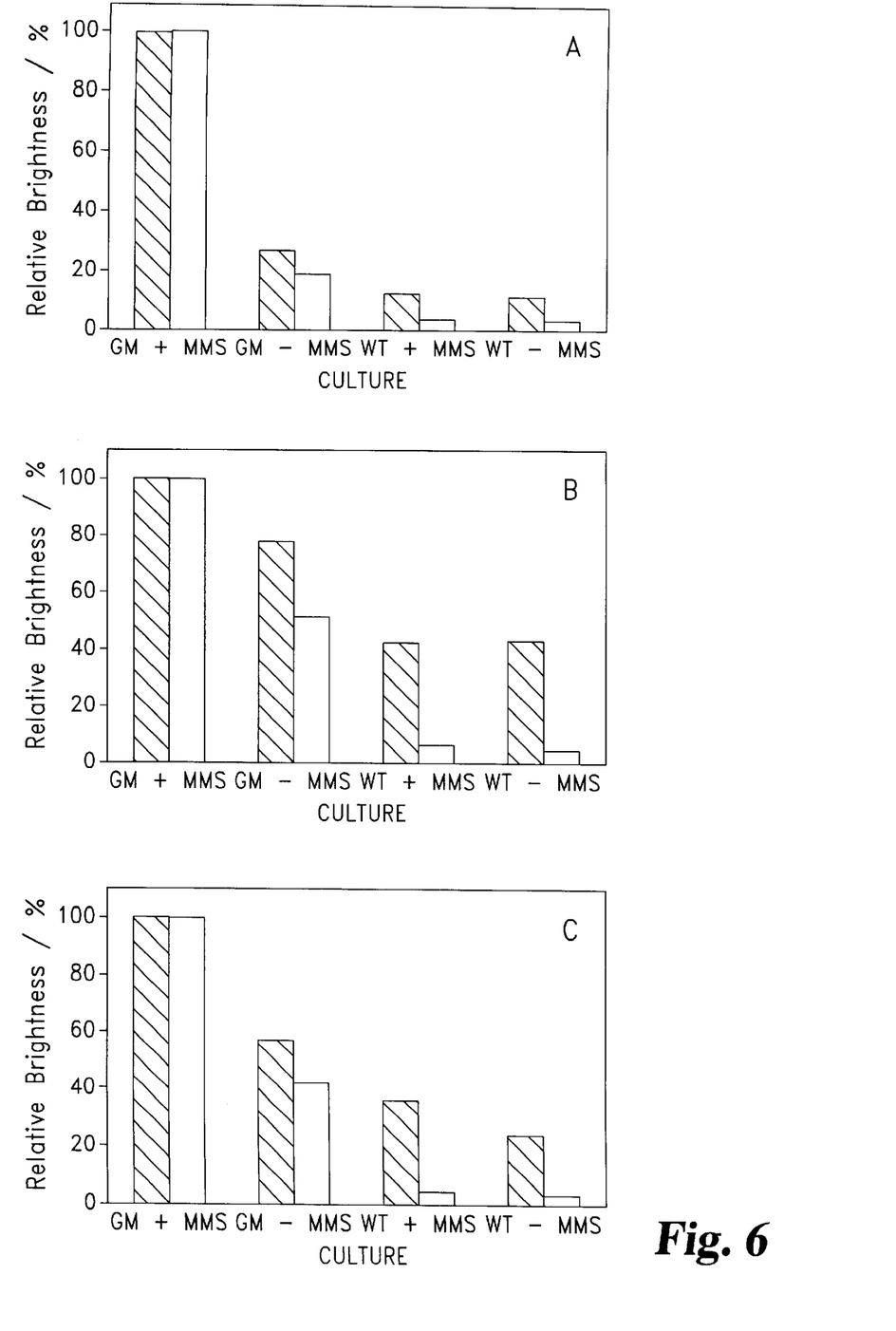
FIG. 6 is a graph comparing the brightness of fluorescence emitted by cultures of genetically modified yeast cells and wild-type yeast cells, as measured using the method according to the first aspect of the invention and as measured using conventional techniques.

To test the polarisation measurement method, GM and wild-type yeast cell cultures of each strain were grown up both in the presence and absence of 0.005% v/v MMS. The brightness of each culture was measured by both the normal fluorescence and fluorescence polarisation methods. FIG. 6 shows the results of the comparative trial, relative brightness measurements obtained using from normal fluorescence are represented by filled in columns, relative brightness measurements obtained using the polarisation dependent method described above are represented by hollow columns. The columns are representative of cultures of genetically modified (GM) and wild-type (WT) cells of each of three strains that were tested. The tested strains were FF18984 (shown in graph A), FY73 (shown in Graph B), and YJL047c (shown in graph C). The columns are scaled such that the brightest culture ("GM+MMS" in which GFP is maximally induced) is 100%.

The use of fluorescence polarisation markedly reduced the auto-fluorescence signal in each case compared to the GFP signal, as evidenced by the wild-type cultures. The GM cells are essentially the same as the wild-type cells except for the added ability to produce GFP, and hence the auto-fluorescence observed in the wild-type cultures will be an intrinsic part of the fluorescence from the GM cells. It should be noted that the GM yeast cells not exposed to the genotoxin are significantly brighter than the wild-type cells. This is due to a near constant background concentration of GFP. The GFP arises from low level expression of Rad54 in the absence of DNA damage, which is only up-regulated when a threshold amount of DNA damage is detected and acted upon. In addition a small amount of DNA damage and associated repair occurs all the time in normal healthy cells. The rate of degradation of GFP in these cells appears to equate with the rate of accumulation under normal conditions, hence the cells generally appear to have a reproducible and stable low level of brightness.

As expected the three different strains induce to different degrees, with induction ratios, as measured by fluorescence polarisation, of 5.40, 1.94 and 2.39 for FF18984, FY73 and YJL047c respectively. The reduction in the auto-fluorescence fraction of the signal for the GM cells resulted in an increase in the apparent "induction ratio". The results quoted represent an increase by an average factor of 1.5 in each strain, for a concentration of 0.005% MMS, when using the fluorescence polarisation method as compared to the conventional fluorescence method.

In general the fluorescence polarisation method of enhancing the signal to background fluorescence ratio should prove more effective at low GFP inductions where the auto-fluorescence forms a greater proportion of the overall fluorescent signal.

Throughout this work "F1" medium has been used for culturing cells due to its extremely low auto-fluorescence. "F1" is a well defined minimal medium made up of 20 separate components including trace elements, vitamins, amino acids and inorganic salts [R. M. Walmsley, D. J. C. Gardner and S. G. Oliver, *Mol. Gen. Genet.*, 1983, 192, 361]. As such it is laborious to prepare, and yeast cultured in it grow much more slowly compared to in a richer media. An investigation was carried out to examine the degree of polarisation of the high auto-fluorescence observed in richer, more complex media, that had so far prevented its use in our in vivo GFP fluorescence studies.

Two media were investigated. Firstly, YEP, a deep yellow rich, complex medium containing; 1% yeast extract and 2% peptone in distilled water. Secondly, YNB, a colourless, minimal, defined medium, containing; 0.67% yeast nitrogen base (without amino acids), 20 mg $l^{-1}$ L-leucine and L-histidine HCl and 30 mg $l^{-1}$ L-lysine HCl in distilled water. Glucose was omitted from each medium sample tested in order to inhibit bacterial contamination growth during the course of the experiment. All media components were obtained from Difco Laboratories, Detroit, Mich., USA, except for the amino acids which were obtained from Sigma-Aldrich.

The fluorescence spectra of both media solutions were obtained using an excitation wavelength of 488 nm. Both were very similar with a broad peak in the 500–600 nm range investigated, with a maximum at approximately 518 nm, thus having considerable spectral overlap with GFP.

To observe similar full-scale fluorescence signals on the fluorescence polarisation instrument, the YEP and YNB media needed to be diluted 10 fold and 3 fold with water respectively.

Each was examined using the continuous flow approach at a flow rate of 1.0 ml $min^{-1}$. From average readings of $I_{\parallel}$ and $I_{\perp}$ the polarisation ratio of the YEP medium was estimated as 0.069 and that of the YNB medium as 0.0069. This represents a signal for $I_{\perp}$ of 87.0 and 98.6% as intense as $I_{\parallel}$ for the YEP and YNB media respectively. Thus, even at 10 times dilution, YEP shows high auto-fluorescence with significant polarisation, precluding its use in our studies without separation of cells and media off-line. The YNB medium however, demonstrated reasonably intense auto-fluorescence but with a low fluorescence polarisation. Hence it is expected that in future work the expression of GFP could be monitored in cells grown in this medium, using the fluorescence polarisation technique, without the need for separation.

In addition to the use of two detectors and two polarising filters with orientations fixed at 90° to each other as illustrated in FIG. 1, the invention may be implemented using a single detector with a single polarising filter. Where this is done, the polarising filter is rotatably mounted. A fluorescence measurement is taken with the polarising filter oriented parallel to the polarisation of light illuminating a sample, and a further fluorescence measurement is taken with the polarising filter oriented perpendicular to the polarisation of the light illuminating the sample. This embodiment of the invention is less expensive than the apparatus shown in FIG. 1 as only a single detector is required. However, use of this embodiment of the invention is more laborious than using the apparatus shown in FIG. 1, since the polarising filter has to be moved between measurements.

In a further alternative embodiment of the invention, a single detector may be used with a single polarising filter that is not rotated between measurements. Instead, two light sources each producing light of a different polarisation are used, a user alternately switching between the light sources to obtain fluorescence measurements for each polarisation.

Although the apparatus shown in FIG. 1 is a flow-through apparatus, it will be understood that the invention may be applied to any suitable apparatus, whether that apparatus is built to allow measurement of fluorescence polarisation, or is modified by the addition of polarising filters. The method may also be applied to applications that produce an image, such as fluorescence microscopy, whereby two images taken using a polarising filter at two different polarisations are digitally or otherwise subtracted. Areas of the image arising from auto-fluorescence will be reduced in intensity to a much greater extent than those areas showing GFP fluorescence.

Figure 7:
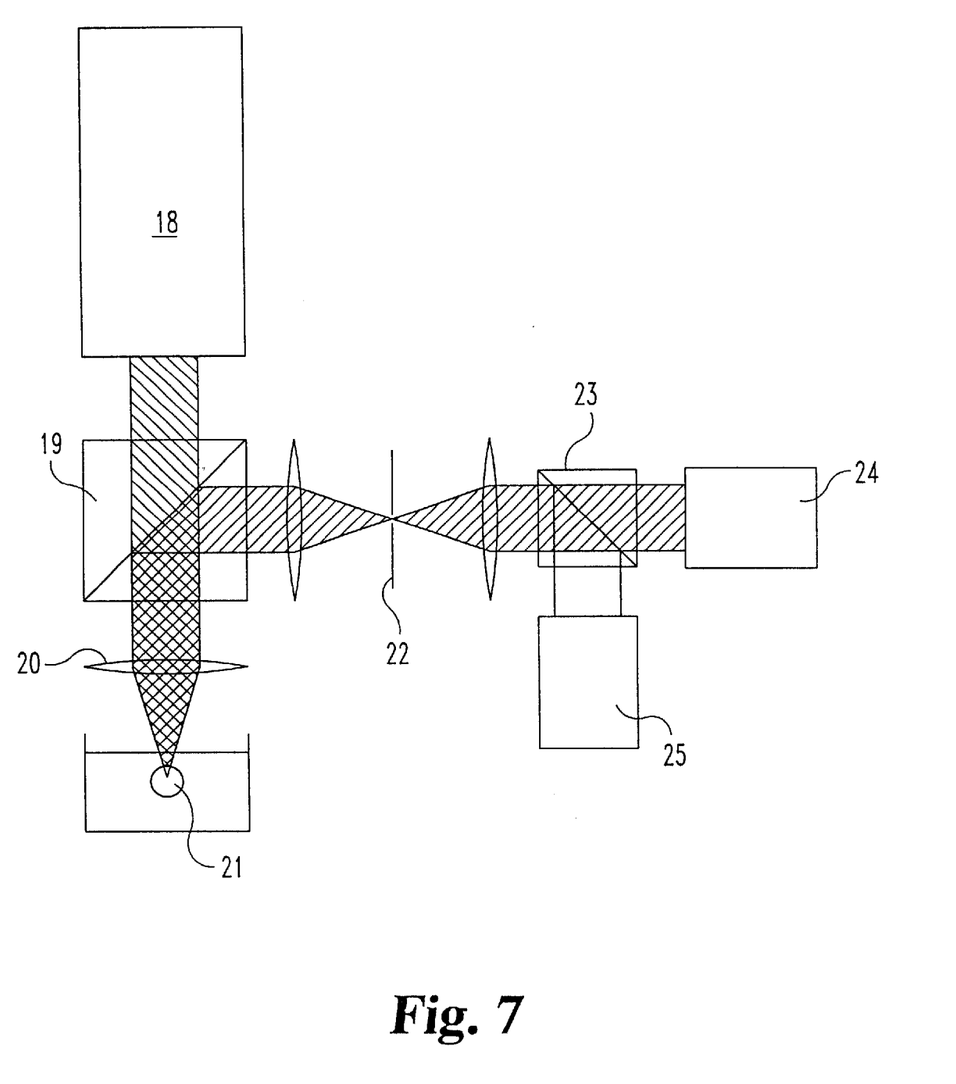
FIG. 7 is a schematic illustration of a confocal fluorescence microscopy apparatus incorporating the invention.

The method according to the invention may be combined with confocal fluorescence microscopy, as illustrated in FIG. 7. Light emitted from a laser 18 passes through a dichroic mirror 19 and is focussed onto a sample 21 by a microscope objective 20. Fluorescent light emitted by the sample is collected by the microscope objective 20, is reflected by the dichroic filter 19 and is spatially filtered from background light by a pinhole 22 (typically a few 100 µm in diameter). A polarising beam splitter 23 (or Wollaston prism) is located behind the pinhole. The polarising beam splitter 23 separates the fluorescent light such that fluorescent light polarised parallel to the laser light is incident upon a first detector 24, and fluorescent light polarised perpendicular to the laser light is incident upon a second detector 25. The signal from the second detector 25 is subtracted from the signal from the first detector 24 to distinguish between fluorescent light emitted by green fluorescent protein and fluorescent light emitted by auto-fluorescent molecules. The wavelength specific filters shown in FIG. 1 may be used as appropriate.

What is claimed is:

1. A method of distinguishing between fluorescent light emitted by green fluorescent protein and fluorescent light emitted by other auto-fluorescent molecules, the method comprising:

using plane-polarized light to illuminate a sample containing green fluorescent protein and other auto fluorescent molecules;

detecting the intensity of fluorescent light that is emitted from said sample with a first polarization from the sample;

detecting the intensity of fluorescent light that is emitted from said sample with a second polarization from the sample;

subtracting a first of said detected intensities from a second of said detecting intensities to obtain a difference signal; and, using the difference signal thus obtained to distinguish between fluorescent light emitted by green fluorescent protein and fluorescent light emitted by other fluorescent molecules in the sample.

2. A method according to claim 1 wherein the first and second polarizations are perpendicular.

3. A method according to claim 1, wherein a polarizing filter is located between the sample and a detector, the intensity of fluorescent light that is emitted with the first polarization being detected by setting the polarizing filter to a first orientation, and the intensity of fluorescent light that is emitted with the second polarization being detected by setting the polarizing filter to a second orientation.

4. A method according to claim 1, wherein the intensity of fluorescent light that is emitted with the first polarization is detected using a first detector, and the intensity of fluorescent light emitted with the second polarization is detected using a second detector.

5. A method according to claim 4, the method further comprising adjusting the first and second detectors such that they provide balanced sensitivities.

6. A method according to claim 5, wherein the sensitivity is adjusted by altering the gain of pre-amplifiers connected to the first and second detectors.

7. A method according to claim 5, wherein the method further comprises illuminating a sample containing molecules that emit fluorescent light having extremely low or no polarization dependency, and adjusting the sensitivity of the first and second detectors, prior to illuminating the sample containing green fluorescent protein and auto-fluorescent molecules.

8. A method according to claim 7, wherein the sample contains 8-hydroxypyrene-1,3,6-trisulfonic acid trisodium salt.

9. A method according to claim 8, wherein the 8-hydroxypyrene-1,3,6-trisulfonic acid trisodium salt is in a solution of suitable pH to enable its fluorescence.

10. A method according to claim 1, wherein the sample is injected periodically into a sample cell, and the illuminating polarized light is directed at the sample cell.

11. A method according to claim 1, wherein the sample is circulated continuously through a sample cell and the illuminating polarized light is directed at the sample cell.

12. A method according to claim 1, wherein detected intensity of fluorescent light is converted into a brightness measurement, by dividing the difference signal by a value corresponding to the density of cells in the sample.

13. A method according to claim 12, wherein the density of cells in the sample is determined by a turbidimetric method.

14. A method according to claim 12, wherein the density of cells in the sample is determined by a nephelometric method.

15. A method according to claim 1, wherein the sample comprises a host cell genetically engineered to express green fluorescent protein.

16. A method according to claim 15, wherein the host cell is a yeast.

17. A method according to claim 15 wherein the green fluorescent protein is expressed in response to DNA damage.

18. A method according to claim 16 wherein the green fluorescent protein is expressed in response to DNA damage.

19. A method according to claim 16 wherein the green fluorescent protein is expressed in response to DNA damage.

* * * * *